(12) United States Patent
Bothorel et al.

(10) Patent No.: US 11,051,774 B2
(45) Date of Patent: Jul. 6, 2021

(54) COMPUTED TOMOGRAPHY APPARATUS AND ASSOCIATED METHOD

(71) Applicant: TROPHY, Marne la Vallee (FR)

(72) Inventors: Sylvie M. Bothorel, Paris (FR); Colombe Maury, Marne la Vallee (FR)

( * ) Notice: Subject to any disclaimer, the term of this patent is extended or adjusted under 35 U.S.C. 154(b) by 0 days.

(21) Appl. No.: 15/524,635

(22) PCT Filed: Nov. 4, 2015

(86) PCT No.: PCT/EP2015/075686
§ 371 (c)(1),
(2) Date: May 5, 2017

(87) PCT Pub. No.: WO2016/071389
PCT Pub. Date: May 12, 2016

(65) Prior Publication Data
US 2017/0319161 A1     Nov. 9, 2017

(30) Foreign Application Priority Data

Nov. 7, 2014     (FR) .................................... 14 60769

(51) Int. Cl.
*A61B 6/00*     (2006.01)
*A61B 6/03*     (2006.01)
(Continued)

(52) U.S. Cl.
CPC ............ *A61B 6/4064* (2013.01); *A61B 6/032* (2013.01); *A61B 6/035* (2013.01); *A61B 6/06* (2013.01);
(Continued)

(58) Field of Classification Search
CPC ......... A61B 6/14; A61B 6/4064; A61B 6/032; A61B 6/035; A61B 6/4007; A61B 6/4266; A61B 6/4435; A61B 6/06
See application file for complete search history.

(56) References Cited

U.S. PATENT DOCUMENTS

| | | | | | |
|---|---|---|---|---|---|
| 4,304,999 | A | * | 12/1981 | Richey | .................... A61B 6/032 378/147 |
| 4,315,157 | A | * | 2/1982 | Barnes | .................... A61B 6/032 378/10 |

(Continued)

FOREIGN PATENT DOCUMENTS

| | | |
|---|---|---|
| EP | 2 240 080 A2 | 10/2010 |
| EP | 2 446 822 A1 | 5/2012 |
| WO | WO 2009/101283 A2 | 8/2009 |

OTHER PUBLICATIONS

International Search Report dated Feb. 24, 2016 for International Patent Application No. PCT/EP2015/075686, 3 pages.

*Primary Examiner* — Chih-Cheng Kao (57) ABSTRACT

The invention relates to a computed tomography radiological apparatus including:
an X-ray source (22) capable of emitting an X-ray beam longitudinally towards an object,
a device (32) for simultaneously splitting the beam into a plurality of beam portions each having a defined propagation direction relative to the longitudinal direction of emission of said X-ray beam,
several sensors (20a-c) intended to receive beam portions which irradiated the object and are arranged transversely side by side relative to the longitudinal direction of the beam, the assembly consisting of X-ray source-splitting device-sensors being capable of turning about an axis of rotation (24) and of adopting different geometric orientations that are angularly shifted with respect to one another in order to, on the one hand, irradiate the object along each one of said geometric orientations of said assembly with the plurality of X-ray beam portions, and, on the other hand, to receive along each one of these geometric orientations the plurality of X-ray beam portions that irradiated the object, the geometric orientation of said assembly being defined by the position of a geometric axis (34) passing, on the one hand, through the focal point (Continued)

of the X-ray source, and, on the other hand, through the axis of rotation (24), the geometric axis (34) having been shifted transversely relative to the center of the plurality of sensors (20*a-c*).

15 Claims, 5 Drawing Sheets

(51) Int. Cl.
*A61B 6/06* (2006.01)
*A61B 6/14* (2006.01)

(52) U.S. Cl.
CPC .............. *A61B 6/14* (2013.01); *A61B 6/4007* (2013.01); *A61B 6/4266* (2013.01); *A61B 6/4435* (2013.01)

(56) References Cited

U.S. PATENT DOCUMENTS

| | | | |
|---|---|---|---|
| 4,481,650 A | | 11/1984 | Kinanen |
| 5,214,686 A | * | 5/1993 | Webber .................... A61B 6/14 378/147 |
| 2005/0152491 A1 | * | 7/2005 | Francke .................. A61B 6/02 378/4 |
| 2010/0278299 A1 | * | 11/2010 | Loustauneau ............ A61B 6/14 378/13 |
| 2011/0176717 A1 | | 7/2011 | Siren et al. |
| 2012/0039435 A1 | | 2/2012 | Arai et al. |
| 2012/0189096 A1 | | 7/2012 | Erhardt et al. |
| 2013/0136226 A1 | | 5/2013 | Tomoe et al. |
| 2014/0247919 A1 | | 9/2014 | Zhang et al. |

\* cited by examiner

Fig. 5

COMPUTED TOMOGRAPHY APPARATUS AND ASSOCIATED METHOD

CROSS REFERENCE TO RELATED APPLICATIONS

This application claims the benefit of and is a U.S. National Phase filing of PCT Application PCT/EP15/75686 filed Nov. 4, 2015 entitled "COMPUTED TOMOGRAPHY APPARATUS AND ASSOCIATED METHOD", in the name of Sylvie M. Bothorel et al, which claims benefit of French Patent application 1460769, filed on Nov. 7, 2014, entitled "COMPUTED TOMOGRAPHY APPARATUS AND ASSOCIATED METHOD", in the name of Sylvie M. Bothorel et al, all of which are incorporated herein in their entirety.

The invention relates to a computed tomography apparatus that can be used in the field of dental radiology, for example.

Conventionally, a computed tomography apparatus used in the dental field consists of an X-ray source and of a sensor, which are mounted opposite one another at each end of a gantry. The sensor is a square or rectangular two-dimensional sensor which has a small ratio between its largest dimension and its smallest dimension. The patient is positioned between the source and the sensor, and the X-ray beam is collimated in such a manner that it passes through an object to be radiographed, such as a dental arch of the patient, or a single tooth. The sensor receives the X-rays that have passed through the object, converts them into electrical signals and thus supplies as output a two-dimensional image of the irradiated object.

The gantry is capable of turning about an axis. Images are obtained for different angular positions of the source and of the sensor relative to the object.

Conventionally, the treatment of these two-dimensional images by algorithms that in themselves are known, such as the FDK algorithms, makes it possible to reconstitute a three-dimensional matrix of absorption coefficients of the object. In order to obtain a three-dimensional image of the object in this manner, it is necessary to produce two-dimensional images over an angular range of at least 180°.

The sensor is an essential component of a radiology apparatus, and its price becomes higher the larger its surface area is. Consequently, many studies have related to the development of techniques allowing the reconstruction of the largest possible three-dimensional images of objects for a given sensor size. In numerous dental computed tomography apparatuses, the sensor is centered relative to the X-ray beam. Thus, the line corresponding to the center of the X-ray beam orthogonally intersects the sensor at its center. The source of rays is point-shaped, and the X-ray beam is in the shape of a cone. According to this geometry, the sensor therefore has to be slightly larger than the object to be reconstituted and of a size similar to the projection of the object on the plane of the sensor. Thus, a sensor plane of dimensions 5 cm×6 cm makes it possible to reconstitute an object whose size is typically 3.2 cm×4 cm.

In the document EP2240080, the sensor is off center relative to the line connecting the point-shaped source of X-rays to the axis of rotation of the gantry. Thus, this line orthogonally intersects the sensor at a point which is shifted relative to its center. An acquisition of two-dimensional images over an angular range of rotation of 360° of the gantry makes possible three-dimensional reconstructions of objects whose projection on the plane of the sensor is larger than the sensor. In particular, the object that it can be reconstituted with a given sensor size is larger than when the sensor is centered.

The document US20120039435 discloses a computed tomography apparatus in the dental field which produces a shift of its axis of rotation along a predetermined path during the acquisition of the data, while the assembly consisting of X-ray source and sensor turns about the axis of rotation. This particular kinematics of the X-ray source and of the sensor makes it possible to increase the size and to modify the shape of the object that can be reconstituted with a source-sensor assembly turning about a fixed axis for a given sensor size.

However, there is a need for the production of a computed tomography apparatus whose cost is not negatively affected by the use of a sensor having large dimensions.

Thus, the invention relates to a radiological apparatus of the computed tomography type, characterized in that it includes:
- at least one X-ray source capable of emitting, along a longitudinal direction, an X-ray beam in the direction of an object to be irradiated,
- a splitting device for simultaneously splitting the X-ray beam into a plurality of X-ray beam portions each having a defined propagation direction relative to the longitudinal direction of emission of said X-ray beam,
- a plurality of sensors which are intended to receive the X-ray beam portions which irradiated the object and which are arranged next to one another in a transverse arrangement relative to the longitudinal direction of the beam, respectively, the assembly formed by said at least one X-ray source, the device for simultaneous splitting of the emitted beam and from an axis of rotation and of adopting different geometric orientations that are angularly shifted one with respect to the other in order to, on the one hand, irradiate the object along each one of said geometric orientations of said assembly with the plurality of X-ray beam portions originating from the X-ray beam, and, on the other hand, to receive along each one of these geometric orientations the plurality of X-ray beam portions that irradiated the object, the geometric orientation of said assembly being defined by the position of a geometric axis passing, on the one hand, through the focal point of said at least one X-ray source, and, on the other hand, through the axis of rotation, the geometric axis having been shifted transversely relative to the center of the transverse arrangement of the plurality of sensors.

This apparatus makes it possible to reduce the costs to the extent that, in order to reconstruct an object in three dimensions by computed tomography, it is not necessary to use a square or rectangular sensor having large dimensions, which is very expensive. Indeed, the splitting of an X-ray beam into several beam portions and the use of several sensors each associated with a portion of the split X-ray beam, by causing the source-splitting device-sensors assembly to turn, makes it possible to acquire all the data necessary for the volume reconstruction of the object or of a portion thereof. Several sensors of reduced dimensions, in comparison to the sensor of larger active surface which would be necessary for this reconstruction, thus considerably reduce the costs of the apparatus. It should be noted that the source-splitting device-sensors assembly can turn in a plane perpendicular to the axis of rotation, for example, and describe a circular path if the axis of rotation is fixed, or describe a helicoidal path about the axis of rotation.

According to other possible features considered separately or in combination with one another:

the geometric axis cuts one of the sensors of the plurality of sensors into two parts, said sensor being either the central sensor of the plurality of sensors in the case where the number of sensors is odd, or one of the two central sensors of the plurality of sensors in the case where the number of sensors is even.

the sensors of the plurality of sensors are spaced transversely from one another in such a manner that two consecutive sensors are spaced by a transverse distance D which is less than the transverse dimension L of each sensor;

the central sensor or one of the two central sensors of the plurality of sensors is cut into a part of width l and a part of width L−l, the widths of said sensor parts satisfying the relation l<(L−D)/2; satisfying this relation makes it possible to ensure that sufficient overlap is obtained with the different X-ray beam portions during the movement of rotation for the different regions of the object to be irradiated (particularly in the central region);

the sensors of the plurality of sensors have, in each case, a general shape that is elongated in a direction parallel to the axis of rotation and have, in each case, a ratio of dimensions in the direction parallel to the axis of rotation and in the transverse direction which is greater than 1.5/1;

the device for simultaneously splitting the X-ray beam into a plurality of X-ray beam portions includes a plurality of parallel slits each capable of allowing the passage of an X-ray beam portion;

the sensors and the slits are arranged in a geometric correspondence in such a manner that each X-ray beam portion originating from a slit of the plurality of slits is received by one sensor of the plurality of sensors;

the slits have, in each case, the same shapes as the sensors;

the slits of the plurality of slits are arranged next to one another in a transverse direction relative to the geometric axis;

the slits are separated transversely from one another by obstacles each of which prevents the propagation of the emitted X-ray beam;

the device for splitting the X-ray beam into a plurality of X-ray beam portions includes a transverse plate perforated by the plurality of parallel slits which are spaced transversely from one another;

the splitting device is arranged between said at least one X-ray source and the object to be irradiated;

the axis of rotation is capable of moving in a direction which is contained in a plane perpendicular to said axis of rotation;

the apparatus includes a unit for the reconstruction of a volume of the irradiated object based on all the X-ray beam portions received which irradiated the object, for at least some of all the different geometric orientations that are angularly shifted relative to one another;

the apparatus is a dental radiology apparatus.

The invention also relates to a method for the acquisition of data pertaining to an object by computed tomography, characterized in that it includes the following steps:

i) emission of an X-ray beam in the direction of an object to be irradiated in a longitudinal direction of emission defining a geometric orientation, ii) simultaneous splitting of the X-ray beam into a plurality of X-ray beam portions each having a defined propagation direction relative to the longitudinal direction of emission of said X-ray beam, iii) irradiation of the object simultaneously with at least some X-ray beam portions originating from the splitting step, iv) reception of X-ray beam portions which irradiated the object.

According to other possible features:

steps i) to iv) reiterated several times, each time angularly shifting, about an axis of rotation, the geometric orientation along which the X-ray beam is emitted and thus the directions of propagation of the beam portions which irradiated the object, the angular shift being considered along a view taken in a plane perpendicular to said axis of rotation;

the method includes a step of reconstruction of a volume of the irradiated object based on the all the received X-ray beam portions which irradiated the object, for at least some of all the geometric orientations of steps i) to iv).

Other features and advantages will become apparent in the following description which is given only as a nonlimiting example and in reference to the appended drawings, in which.

Figure 1:
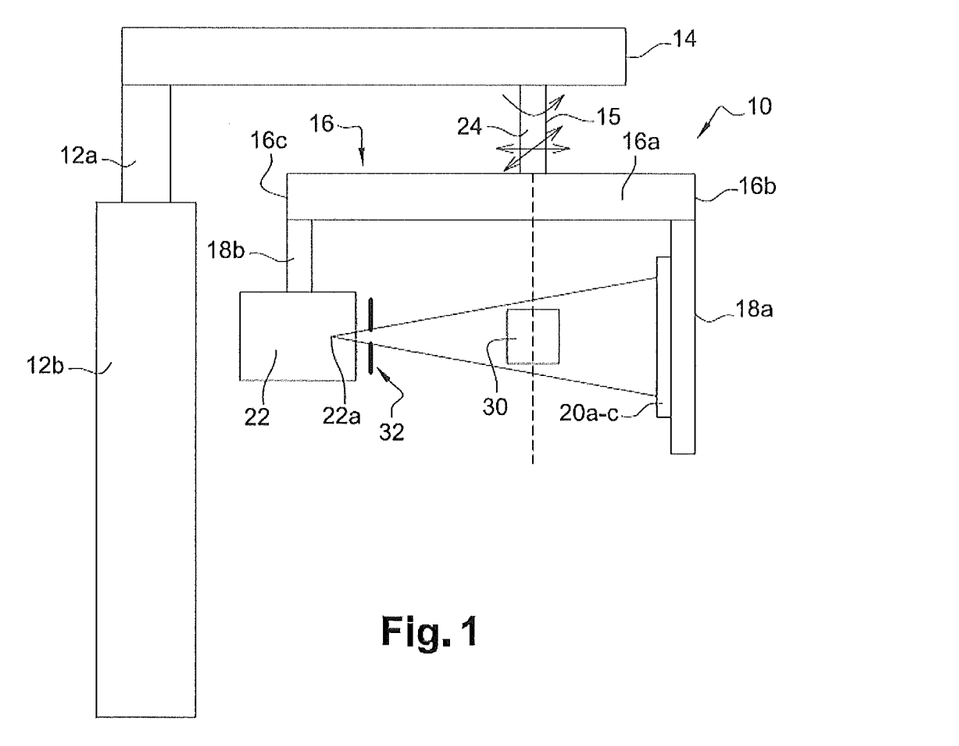
FIG. 1 is a diagrammatic view of a dental computed tomography apparatus according to an embodiment of the invention.

The computed tomography apparatus 10 (known in English terminology under the term "computed tomography") according to an embodiment of the invention is a radiological computed tomography apparatus which is of the cone beam type (known in English terminology under the term "cone beam computed tomography"), for example. The apparatus includes a column 12 supporting a horizontal arm 14 (FIG. 1). The column can be telescopic and, for example, include an upper portion 12a sliding inside a lower portion 12b. The arm 14 is thus supported by the upper end of the upper portion 12a.

The arm 14 supports, by means of a rotary shaft 15, a gantry 16 (known in the English terminology under the term "gantry"), which includes a horizontal beam 16a provided at each one of its two opposite ends 16b, 16c with two vertical arms 18a, 18b facing one another. Each vertical arm extends downward from the end of the beam to which it is connected and functions as support for part of a data acquisition apparatus. Thus, the arm 18a supports a plurality of sensors 20a-c, and the arm 18b supports an X-ray source 22 which is arranged opposite the plurality of sensors.

The gantry 16 is capable of turning about a vertical axis of rotation 24 which corresponds to the axis of rotation of the rotary shaft 15. During this rotation, the source 22 and the plurality of sensors 20a-c are turned about the axis of rotation 24 and describe a circular path in a plane perpendicular to the axis 24. Appropriate control means for controlling the movement of the gantry 16 (not represented and known in themselves) are provided for this purpose. The axis of rotation 24 can also be shifted, while remaining parallel to itself, in a direction perpendicular to the axis, and which is contained in the plane of rotation of the source and of the sensors following a predetermined path. This path is obtained by an appropriate instruction delivered by the above-mentioned control means.

Figure 2A:
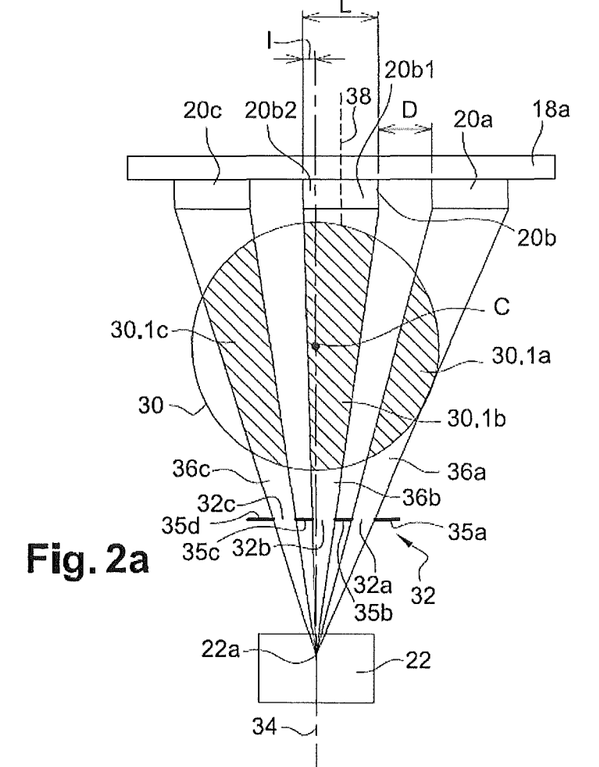
FIGS. 2a-d are top views showing the arrangement of the X-ray source, of the device for splitting the X-ray beam which is positioned in front of the source, and of the plurality of sensors, as well as the volumes of the area of interest irradiated by the plurality of X-ray beams at each angular position of the source-sensor assembly.

It should be noted that the X-ray beam is emitted by the source 22 in the direction of a patient (object to be irradiated), in a longitudinal direction which is parallel to the plane in which the source 22 and the sensors 20*a-c* move. The longitudinal direction of the beam is defined by the geometric axis 34 which passes through the focal point 22*a* of the source 22 and through the axis of rotation 24 which it intersects perpendicularly at a point referred to as the center of rotation C (FIG. 2*a*).

When the apparatus 10 is used, the patient is positioned between the source 22 and the plurality of sensors 20*a-c*. The apparatus 10 is intended to reconstruct an area of interest 30 of the patient which can be, for example, the entire head of the patient in the case of apparatuses that offer the possibility of a large field size, his/her dentition including the two dental arches, a single dental arch, a dental arch portion, a single tooth or two opposite teeth. For specific applications, the area of interest 30 can correspond to the sinuses of the patient, to the condyles or to the temporomandibular joint.

The apparatus 10 also includes a splitting device 32 whose function is to simultaneously split the X-ray beam emitted by the source 22 into a plurality of X-ray beam portions. The splitting device 32 is arranged between the source 22 and the area of interest 30 of the object to be irradiated and, for example, is placed in front of the source 22, at a distance between 1 cm and 10 cm. The splitting device 32 is subjected to the same shifting as the source 22. For the sake of convenience, the device 32 can be mechanically attached to the source 22 or directly to the arm 18*b*.

As illustrated in FIGS. 2*a*, 2*b*, 2*c* and 2*d*, the splitting device 32 includes a plurality of slits or openings 32*a-c* parallel to one another, each of which has a vertical elongated shape (parallel to the axis of rotation 24). The slits are arranged next to one another in a transverse direction perpendicular to the geometric axis 34 (longitudinal direction of emission of the X-ray beam) and separated from one another and/or framed by obstacles or screens 35*a-d*. These slits confer to the splitting device 32 the function of a collimator and form, from the X-ray beam emitted by the source 22, a plurality of X-ray beam portions referenced 36*a*, 36*b* and 36*c* which are vertically elongated just like the slits themselves. Each of the obstacles or screens 35*a-d* prevents the propagation of the X-ray beam portions emitted by the source 22 that collide with said obstacles or screens, these portions being located between the portions 36*a*, 36*b*, 36*c*. Each of the X-ray beam portions 36*a*, 36*b* and 36*c* represented in FIGS. 2*a-d* has a defined direction of propagation relative to the longitudinal direction of emission of said X-ray beam forming a defined angle relative to this longitudinal direction (geometric axis 34).

The number of slits illustrated in this embodiment is three. However, this number can be different from three in variants that are not represented. This number is, however, at least equal to two. The slits 32*a*, 32*b* and 32*c* of the collimator are dimensioned and positioned in such a manner that the beams 36*a*, 36*b* and 36*c* which they form are received by the sensors 20*a*, 20*b*, 20*c* of the plurality of sensors. It should be noted that the number of sensors corresponds to the number of slits.

The sensors are themselves also arranged transversely next to one another in a transverse alignment parallel to the transverse alignment of the slits. The sensors have, in each case, a vertically elongated shape and their dimensions are adapted so that each receives the entire beam portion transmitted by the associated slit (slit in geometric correspondence with the sensor). The shapes of the slits and of the sensors are identical and their dimensions are homothetic.

The use of a plurality of sensors of reduced size associated with the device for splitting the X-ray beam into a corresponding plurality of X-ray beam portions makes it possible to avoid having to use a sensor of large size whose dimensions would correspond to those of the emitted beam.

The three sensors 20*a-c* are all positioned asymmetrically relative to the geometric axis 34 (FIG. 2*a*). Thus, the central sensor 20*b* is positioned on the support arm 18*a* in such a manner that it is located mainly on one side of the axis 34 (the position of the center of the sensor illustrated by the axis 38 in FIG. 2*a* shows an offset relative to the geometric axis 34), with a main portion 20*b*1 on this side of the axis and the remaining portion 20*b*2 of the sensor located on the other side of this axis.

In practice, the width of the sensitive area of the sensor is referenced L (in the figures only the sensitive areas of the sensors are represented), and the width l of the remaining portion 20*b*2 of the sensor located to the left of the axis 34 in FIG. 2*a* is less than the width L.

As represented in FIG. 2*a*, the sensors 20*a-c* are spaced transversely from one another in such a manner that the sensitive areas of two consecutive sensors are separated from one another by the same distance D which is less than the width L of the sensitive area of each sensor.

Figure 3:
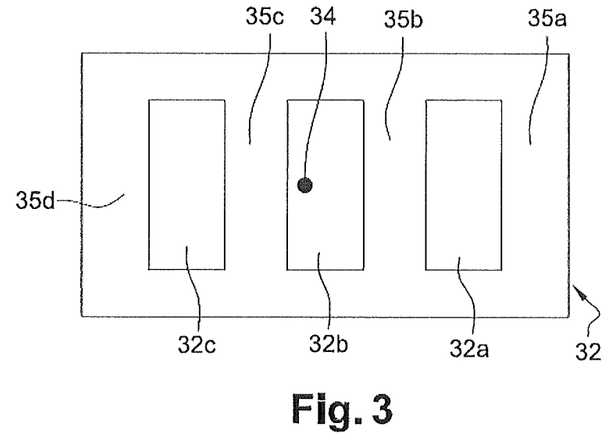
FIG. 3 is a diagrammatic view of a device for splitting an X-ray beam according to an embodiment of the invention.

An example of a beam splitting device is represented in FIG. 3 in the form of a plate 32 made of lead, for example, arranged transversely relative to the longitudinal direction of the beam (geometric axis 34). The plate is perforated in its thickness by a plurality of rectangular slits 32*a-c* parallel to one another and spaced from one another by the plate portions forming obstacles or screens for the beam 35*a-d*.

When the apparatus 10 is programmed in order to acquire radiological data pertaining to the area of interest 30 of a patient, the gantry 16 turns about the axis of rotation 24 by performing a rotation or scan ("scan" in the English terminology) of 360°, thus driving by its movement the assembly formed by the source 22, the splitting device 32 and the sensors 20*a-c*, which describes a circle in the plane of rotation (plane of FIG. 2*a*).

Figure 4:
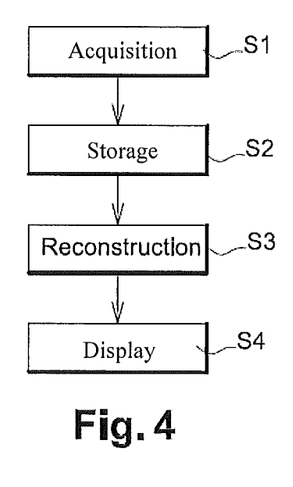
FIG. 4 is a diagrammatic view of a flowchart illustrating the steps of a data acquisition and image reconstruction method according to an embodiment of the invention.

It should be noted that the apparatus is programmed, in particular, for implementing the method whose algorithm/flow chart is illustrated in FIG. 4 and whose first step S1 corresponds to the acquisition of data by the apparatus 10.

The portions 36*a*, 36*b* and 36*c* of the X-ray beam, which are transmitted simultaneously through the slits 32*a*, 32*b* and 32*c*, pass through the area of interest 30 for each angular position of the gantry 16 relative to the patient and this for a plurality of angular positions different from one another. Each of these angular positions is obtained by a rotation of the assembly formed by the source 22, the splitting device 32 and the sensors 20*a-c* by one or more degrees relative to the preceding position.

Each angular position of the gantry 16 is characterized by an angular or geometric position of the assembly formed by the source 22, the splitting device 32 and the sensors 20*a-c* and, more particularly, by the position or the geometric orientation of the geometric axis 34 in the plane of rotation of this assembly (plane of FIGS. 2a-d).

Figure 2B:
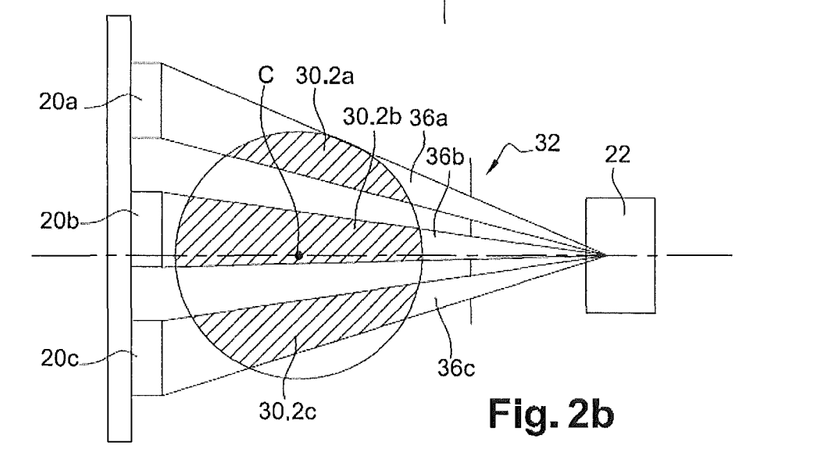

Thus, for a first reference angular position (FIG. 2a), the beam portions 36a, 36b and 36c irradiate the volumes 30.1a, 30.1b and 30.1c of the area of interest 30, respectively. A second angular position of the gantry relative to the patient is illustrated in FIG. 2b and corresponds to a rotation over an angle of 90° relative to the reference position of FIG. 2a. In this position, the beams 36a, 36b and 36c irradiate the volumes 30.2a, 30.2b and 30.2c, which are different from the volumes irradiated in the first reference angular position.

Figure 2C:
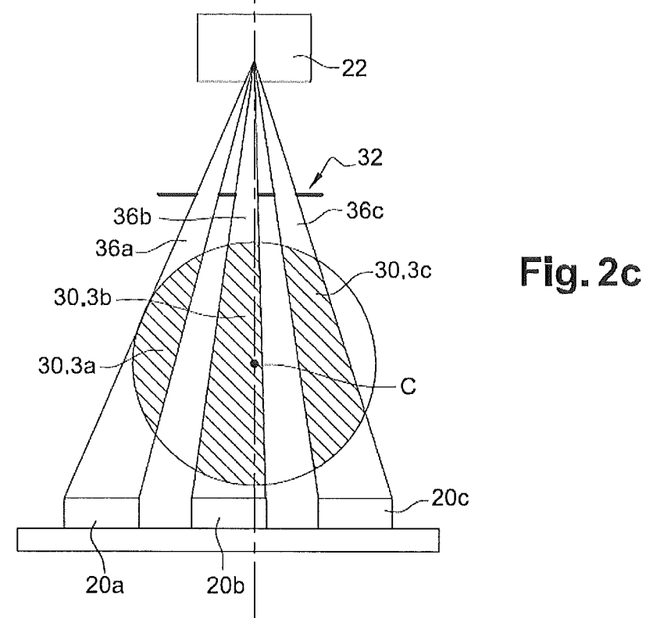
Figure 2D:
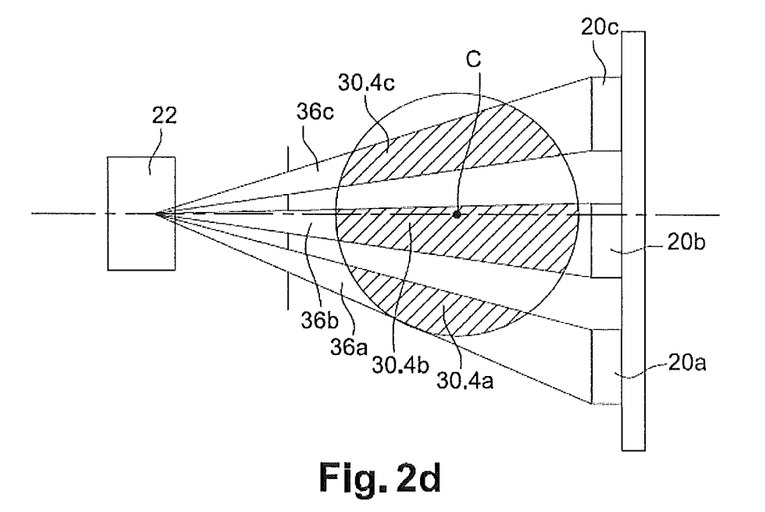

FIGS. 2c and 2d correspond to the irradiation of the area of interest 30 at the angularly positions shifted by 180° and 270°, respectively, relative to the reference angular position of FIG. 2a. In the angular position of FIG. 2c (respectively FIG. 2d), the beams 36a, 36b and 36c irradiate the volumes 30.3a, 30.3b and 30.3c (respectively the volumes 30.4a, 30.4b and 30.4c), which are different from the irradiated volumes in the preceding angular positions.

The fact that there is a portion 20b2 of the central sensor 20b of width 1 on one side of the axis 34 relative to the remaining portion 20b1 of larger width located on the other side of this axis makes it possible to obtain an overlapping of the irradiated central region (in the area of interest 30) for diametrically opposite angular positions of the gantry 16. Thus, there is overlap in the central region of the area of interest 30 for the beam portions 30.1b (FIG. 2a) and 30.3b (FIG. 2c), on one hand, and for the beam portions 30.2b (FIG. 2b) and 30.4b (FIG. 2d), on the other hand. This region or area of overlap makes it possible to get a smooth transition between the data obtained in the case of diametrically opposite angular positions and to limit the artifacts on the reconstructed three-dimensional image.

One should note in particular that in practice an overlap is needed between the right end of the beam portion 30.1c (FIG. 2a) and the left end of the beam portion 30.3b (FIG. 2c). This means that the left end of the sensor 20c (FIG. 2a) which is at distance D+1 from the geometric axis 34 has to be closer to the axis 34 than the left end of the sensor 20b (FIG. 2c) which is at distance L−1 from the axis. In other words, the distance D+1 is less than the distance L−1, which is equivalent to saying that the width 1 is less than (L−D)/2.

The fact that the distance D (FIG. 2a) between the sensitive areas of the consecutive sensors two-by-two is smaller than the width of the sensitive areas themselves makes it possible to irradiate the entire volume of the area of interest 30 during a complete rotation of the above-mentioned assembly in the plane of rotation, with a certain degree of overlapping which makes it possible to smoothen the transitions between the regions irradiated at different angles or geometric positions of the geometric axis 34.

The scan is achieved by acquiring a plurality of data that are representative of two-dimensional images of the area of interest 30 by irradiation of this area in each angular position of the gantry 16 (corresponding to an angular position of the geometric axis 34 in the plane of rotation) over the angular range 0-360°.

It should be noted that the angular positions of data acquisition correspond to angular positions defined regularly by increments of 0.5° or 1° typically over the entire range of 0-360°.

The plurality of X-ray beam portions 36a-c which have passed through the area of interest 30 (for example: dental arch of the patient) are received by the plurality of sensors 20a-c, respectively, each of which converts the rays received into electrical signals in order to form a two-dimensional image. The images are then recorded in one or more storage areas of the apparatus 10, which are not represented, in accordance with step S2 of FIG. 4. Typically, several hundreds of two-dimensional images are thus recorded. The angular pitch between two successive two-dimensional images is between 0.5° and 1°, for example.

Using the above-described apparatus, in particular, due to the arrangement of the slits and of the sensors, after a complete scan of the area of interest 30 has been performed, each volume element of the area of interest 30 has been passed through by rays in all the possible directions in the plane of the path of the X-ray source and of the sensor.

Indeed, this is a necessary condition for the reconstruction of an image in three dimensions of the area of interest.

A three-dimensional image in the form of a matrix of absorption coefficients is then reconstructed by computation using an FDK type algorithm adapted to the above-described geometry (step S3 of FIG. 4). The adaptations include the following steps/operations:

Weighting of the redundant rays. The weighting function applied varies continuously and regularly from 0% to 100%.

Filling of the truncated projections. The FDK type algorithm includes passing a frequency filter. Normally passaging this filter involves a nontruncated objects. The fact of having truncated projections (which happens each time an object extends beyond the edges of the sensor) creates so-called "truncated projection" artifacts. These artifacts conventionally can be decreased by adding information to the edges of the projections at the time of the application of the filter. In the case of the geometry described above, one can add the information that is missing between the sensors by using the rays of opposite projections.

Once the three-dimensional image has been reconstructed, it is displayed, for example, on a display screen (not represented) associated with the apparatus 10 (step S4 of FIG. 4).

Figure 5:
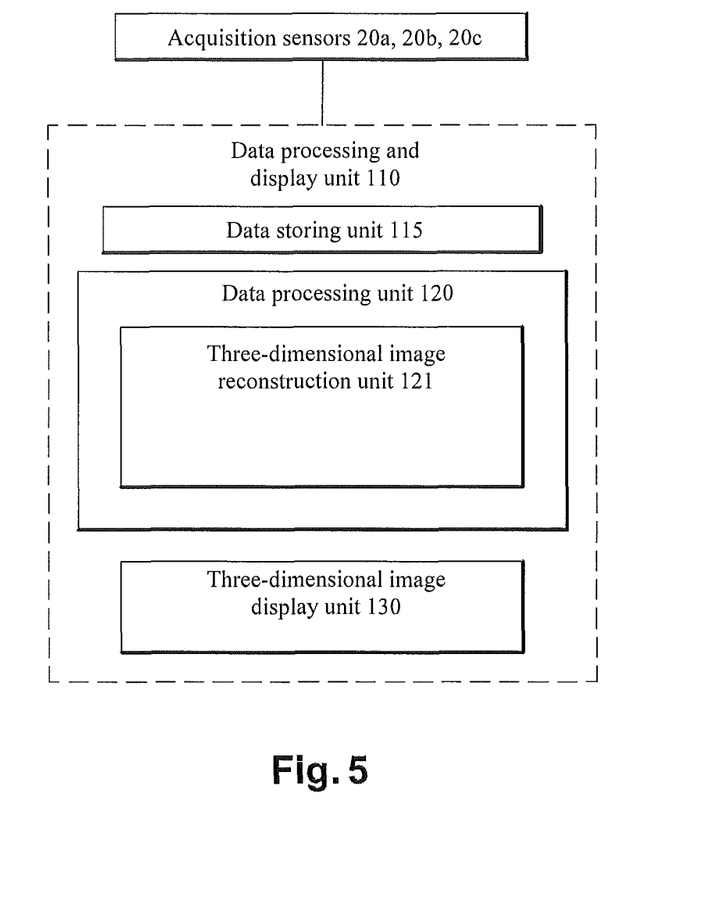
FIG. 5 is a diagrammatic view of a data acquisition and image reconstruction system which is part of the apparatus of FIG. 1.

FIG. 5 represents very diagrammatically a data acquisition and image reconstruction system that is part of the apparatus 10 of FIG. 1.

This system includes the plurality of sensors 20a-c (data acquisition sensors) which acquire the data as described above. These data are then transmitted to a data processing and display unit 110 which includes:
  a data storing unit 115 which consists of one or more memory areas of a storage space, for example;
  a data processing unit 120 which consists of a microprocessor, for example, this unit 120 itself including a three-dimensional image reconstruction unit 121,
  a three-dimensional image display unit 130.

Although the invention has been described above with a geometry according to which the axis of rotation 34 is stationary, it is entirely possible to consider an axis of rotation that is moveable during the scan. The axis of rotation then describes a predefined path, for example, in the plane of rotation which is perpendicular to said axis, during the scan at the same time as the gantry 16 turns about this axis. In particular, the axis 34 can describe a back and forth movement along a horizontal axis. The axis 34 can also describe a two-dimensional path in a plane perpendicular to this axis. The source 22 and the sensors 20a, 20b, 20c then have a movement which is the combination of a rotation and of a translation.

According to a variant which is not represented, the assembly consisting of the source, the splitting device and the sensors turns about the axis of rotation describing a helicoidal path centered about this axis. In practice, this movement is obtained by a combination of a movement of rotation about the axis of rotation 24 of the assembly consisting of the source, the splitting device and the sensors, and a vertical translation (rise or fall in FIG. 1) of this assembly along the axis.

According to a variant which is not represented, the X-ray beam emitted by the source 22 is not conical but in the shape of a fan (known under the term "fan beam" in the English terminology) viewed in the plane of FIGS. 2*a*-*d*. Such a beam has a low height (considered perpendicularly to the plane of FIGS. 2*a*-*d*) compared to the width of the beam in the plane, typically in a width-height ratio of at least 10/1. With this beam configuration, each of the slots and of the sensors has an adapted geometric shape which is either square or rectangular. In the case of a rectangular shape, the length of the rectangle, extends in the plane of FIGS. 2*a*-*d* and its width corresponds to the height of the beam.

According to a variant which is not represented, the number of sensors of the plurality of sensors is even. In this case, the geometric axis 34 of the FIGS. 2*a*-*d* cuts one of the two sensors arranged at the center of the arrangement of the sensors into two parts, as with the parts 20*b*1 and 20*b*2 of the central sensor 20*b* in FIG. 2*a*.

The invention claimed is:

1. Radiological apparatus of the computed tomography type, characterized in that it includes:
   at least one X-ray source (22) capable of emitting, along a longitudinal direction, an X-ray beam in the direction of an object to be irradiated (30),
   a splitting device (32) for simultaneously splitting the X-ray beam into a plurality of X-ray beam portions (30.1*a*-*c*) each having a defined propagation direction relative to the longitudinal direction of emission of said X-ray beam,
   a plurality of sensors (20*a*-*c*) which are intended to receive the X-ray beam portions which irradiated the object and which are arranged next to one another in a transverse arrangement relative to the longitudinal direction of the beam, respectively, the assembly formed by said at least one X-ray source, the device for simultaneous splitting of the emitted beam and the plurality of sensors being capable of turning about an axis of rotation (24) and of adopting different geometric orientations that are angularly shifted one with respect to one another in order to, on the one hand, irradiate the object along each one of said geometric orientations of said assembly with the plurality of X-ray beam portions originating from the X-ray beam, and, on the other hand, to receive along each one of these geometric orientations the plurality of X-ray beam portions that irradiated the object, the geometric orientation of said assembly being defined by the position of a geometric axis (34) passing, on the one hand, through the focal point of said at least one X-ray source, and, on the other hand, through the axis of rotation (24), the geometric axis (34) having been shifted transversely relative to the center of the transverse arrangement of the plurality of sensors (20*a*-*c*),
   characterized in that the geometric axis (34) cuts one of the sensors of the plurality of sensors (20*a*-*c*) into two unequal parts during a single imaging exposure, said sensor being either the central sensor (20*b*) of the plurality of sensors in the case where the number of sensors is odd, or one of the two central sensors of the plurality of sensors in the case where the number of sensors is even,
   where the sensors of the plurality of the sensors (20*a*-*c*) are spaced transversely from one another in such a manner that two consecutive sensors are spaced by a transverse distance (D) that is less than the transverse dimension (L) of each sensor and the central sensor or one of the two central sensors of the plurality of sensors is cut into a part of width l and a part of width L−l, the widths of said sensor parts satisfying the relation l<(L−D)/2.

2. Apparatus according to any one of claim 1, characterized in that the sensors of the plurality of sensors (20*a*-*c*) have, in each case, a general shape that is elongated in a direction parallel to the axis of rotation (24) and have, in each case, a ratio of dimensions in the direction parallel to the axis of rotation (24) and in the transverse direction which is greater than 1.5/1.

3. Apparatus according to any one of claim 1, characterized in that the device (32) for simultaneously splitting of the X-ray beam into a plurality of X-ray beam portions includes a plurality of parallel slits (32*a*-*c*) each capable of allowing the passage of an X-ray beam portion.

4. Apparatus according to claim 3, characterized in that the sensors (20*a*-*c*) and the slits (32*a*-*c*) are arranged in a geometric correspondence to one another in such a manner that each X-ray beam portion originating from a slit of the plurality of slits is received by one sensor of the plurality of sensors.

5. Apparatus according to claim 3, characterized in that the slits (20*a*-*c*) have, in each case, the same shapes as the sensors (32*a*-*c*).

6. Apparatus according to claim 3, characterized in that the slits of the plurality of slits (32*a*-*c*) are arranged next to one another in a transverse direction relative to the geometric axis (34).

7. Apparatus according to claim 6, characterized in that the slits (32*a*-*c*) are separated transversely from one another by obstacles each preventing the propagation of the emitted X-ray beam.

8. Apparatus according to claim 3, characterized in that the device (32) for splitting the X-ray beam into a plurality of X-ray beam portions includes a transverse plate perforated by the plurality of parallel slits spaced transversely from one another.

9. Apparatus according to claim 1, characterized in that the splitting device (32) is arranged between said at least one X-ray source (22) and the object to be irradiated (30).

10. Apparatus according to claim 1, characterized in that the axis of rotation (24) is capable of moving in a direction which is contained in a plane perpendicular to said axis of rotation.

11. Apparatus according to claim 1, characterized in that it includes a unit (121) for the reconstruction of a volume of the irradiated object based on all the X-ray beam portions received which irradiated the object, for at least some of all the different geometric orientations that are angularly shifted relative to one another.

12. Apparatus according to claim 1, characterized in that the apparatus is a dental radiology apparatus.

13. Method for the acquisition of data pertaining to an object by computed tomography, characterized in that it includes the following steps:
   i) emission of an X-ray beam in the direction of an object to be irradiated (30) in a longitudinal direction of emission,
   ii) simultaneous splitting of the X-ray beam into a plurality of X-ray beam portions each having a defined propagation direction relative to the longitudinal direction of emission of said X-ray beam,
iii) reception of the X-ray beam portions at a plurality of sensors (32a-c) arranged next to one another in a transverse arrangement relative to the longitudinal direction of the beam, and
iv) reconstruction of a volume image based on the received X-ray beam portions for at least some of different geometric orientations that are angularly shifted relative to one another relative to an axis of rotation, characterized in that a center of the X-ray beam portions cuts one of the sensors of the plurality of sensors (32a-c) into two unequal parts during a single imaging exposure, said sensor being either the central sensor (20b) of the plurality of sensors in the case where the number of sensors is odd, or one of the two central sensors of the plurality of sensors in the case where the number of sensors is even, where the sensors of the plurality of the sensors (32a-c) are spaced transversely from one another in such a manner that two consecutive sensors are spaced by a transverse distance (D) that is less than the transverse dimension (L) of each sensor and the central sensor or one of the two central sensors of the plurality of sensors is cut into a part of width l and a part of width L−l, the widths of said sensor parts satisfying the relation l<(L−D)/2.

14. Method according to claim 13, characterized in that the steps i) to iii) are reiterated several times, each time angularly shifting, about an axis of rotation (24), a geometric orientation (34) along which the X-ray beam is emitted and thus the directions of propagation of the beam portions that irradiated an object, the angular shift being considered along a view taken in a plane perpendicular to said axis of rotation.

15. Method according to claim 14, characterized in that it includes a step of reconstruction of a volume of the irradiated object based on all the X-ray beam portions received that irradiated the object for at least some of all the geometric orientations of steps i) to iii).

* * * * *